US012797237B2

(12) United States Patent
Mitchell et al.

(10) Patent No.: US 12,797,237 B2
(45) Date of Patent: Nov. 17, 2026

(54) TIP VALVE FOR EYE DROP DISPENSER

(71) Applicant: Alcon Inc., Fribourg (CH)

(72) Inventors: Jeffrey Thomas Mitchell, Mansfield, TX (US); Stephen J. Van Noy, Southlake, TX (US)

(73) Assignee: Alcon Inc., Fribourg (CH)

( * ) Notice: Subject to any disclaimer, the term of this patent is extended or adjusted under 35 U.S.C. 154(b) by 359 days.

(21) Appl. No.: 18/489,153

(22) Filed: Oct. 18, 2023

(65) Prior Publication Data

US 2024/0148550 A1 May 9, 2024

Related U.S. Application Data

(60) Provisional application No. 63/382,907, filed on Nov. 9, 2022.

(51) Int. Cl.
*A61F 9/00* (2006.01)

(52) U.S. Cl.
CPC .................................. *A61F 9/0026* (2013.01)

(58) Field of Classification Search
CPC ...... A61F 9/0026; A61F 9/0008; F16K 23/00; A61J 1/067; B65D 47/2031; B65D 47/205; B65D 47/18; B65D 47/2081; B65D 47/2068; B65D 1/023; B65D 25/40; B65D 25/48; B65D 2547/063; B05B 11/0032; B05B 11/007; B05B 11/047; B05B 11/0072; B05B 11/00
See application file for complete search history.

(56) References Cited

U.S. PATENT DOCUMENTS

| | | | |
|---|---|---|---|
| 5,092,855 | A | 3/1992 | Pardes |
| 5,863,562 | A | 1/1999 | Tsao |
| 6,695,173 | B1 | 2/2004 | Fontana |
| 7,874,467 | B2 | 1/2011 | Pardes |
| 8,382,010 | B2 | 2/2013 | Nadler |
| 9,174,777 | B2 | 11/2015 | Defemme |
| 9,339,375 | B2 | 5/2016 | Lee |
| 9,402,765 | B2 | 8/2016 | Chibret |
| 9,833,356 | B2 | 12/2017 | Wochele |
| 10,538,369 | B2 | 1/2020 | Ritsche |

(Continued)

FOREIGN PATENT DOCUMENTS

| | | |
|---|---|---|
| BR | PI0414025 A | 10/2006 |
| RU | 81433 U1 | 3/2009 |

*Primary Examiner* — Guy K Townsend
*Assistant Examiner* — Alessandro R Del Priore
(74) *Attorney, Agent, or Firm* — Nicholas Smith

(57) ABSTRACT

An eye dropper includes a nozzle secured to a reservoir. The nozzle includes a sleeve that extends around the center and has a first zone, a second zone, and a third zone, having corresponding first, second, and third expansion pressures at which the first, second and third zones separate from the center. The second pressure is less than the first expansion pressure and the third expansion pressure is less than the second expansion pressure. The third expansion pressure may be less than the first expansion pressure. A notch in the sleeve may receive a ridge on the center. The zones may be positioned over a groove in the center or extend completely around a center that is cylindrical or frusto-conical in shape. Multiple instances of first, second and third zones may be distributed along the center. The sleeve may be made of a more flexible material than the center.

14 Claims, 6 Drawing Sheets

(56) References Cited

U.S. PATENT DOCUMENTS

| | | | | |
|---|---|---|---|---|
| 10,640,268 | B2 | 5/2020 | Painchaud | |
| 11,033,922 | B2 | 6/2021 | Julia | |
| 11,235,914 | B2 | 2/2022 | Pozzi | |
| 11,319,121 | B2 | 5/2022 | Painchaud | |
| 11,365,031 | B2 | 6/2022 | Pozzi | |
| 11,679,028 | B2 | 6/2023 | Quintana | |
| 2003/0173380 | A1 * | 9/2003 | Gerber | B65D 47/205 222/519 |
| 2004/0200860 | A1 | 10/2004 | Buxmann | |
| 2005/0173459 | A1 | 8/2005 | Buxmann | |
| 2007/0093765 | A1 | 4/2007 | Kawashiro | |
| 2007/0095862 | A1 | 5/2007 | Swiss | |
| 2009/0152306 | A1 * | 6/2009 | Pardes | A61M 11/008 137/846 |
| 2009/0236374 | A1 | 9/2009 | Pardes et al. | |
| 2011/0130833 | A1 | 6/2011 | Scott et al. | |
| 2014/0301875 | A1 | 10/2014 | Lee | |
| 2015/0150719 | A1 | 6/2015 | Chibret | |
| 2017/0029175 | A1 | 2/2017 | Decock | |
| 2017/0120272 | A1 | 5/2017 | Decock | |
| 2018/0078455 | A1 | 3/2018 | Defemme | |
| 2018/0078456 | A1 | 3/2018 | Defemme | |
| 2020/0223599 | A1 | 7/2020 | Painchaud | |
| 2020/0262622 | A1 | 8/2020 | Wochele | |
| 2021/0322209 | A1 | 10/2021 | Ivri | |

* cited by examiner

TIP VALVE FOR EYE DROP DISPENSER

BACKGROUND

Many pathologies of the eye are treated by direct application of drops of liquid to the eye ("eye drops"). For example, conjunctivitis is treated by directly applying eye drops containing antibiotics. Dry eyes and glaucoma are also treated using eye drops. An eye drop dispenser contains multiple doses and therefore must be used repeatedly over many days. It is therefore important to reduce the entry of contaminants into the dispenser.

BRIEF SUMMARY

The present disclosure relates generally to a nozzle for a dispenser of eye drops.

A nozzle for an eye drop dispenser includes a center configured to affix to a reservoir at a proximal end of the center and having a distal end opposite the proximal end. A sleeve extends around the center and has a first zone, a second zone, and a third zone, the first zone being positioned closer to the proximal end than the second zone and the third zone being positioned closer to the distal end than the second zone. At least a portion of the first zone has a first expansion pressure at which the at least the portion of the first zone will separate from the center such that fluid can flow between the at least the portion of the first zone and the center. At least a portion of the second zone has a second expansion pressure at which the at least the portion of the second zone will separate from the center such that the fluid can flow between the at least the portion of the second zone and the center. At least a portion of the third zone has a third expansion pressure at which the at least the portion of the third zone will separate from the center such that the fluid can flow between the at least the second zone and the center. The second expansion pressure is less than the first expansion pressure, and the third expansion pressure is less than the second expansion pressure.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a nozzle for an eye dropper that reduces or prevents contamination of fluid in a reservoir that is dispensed through the nozzle.

Figure 1:
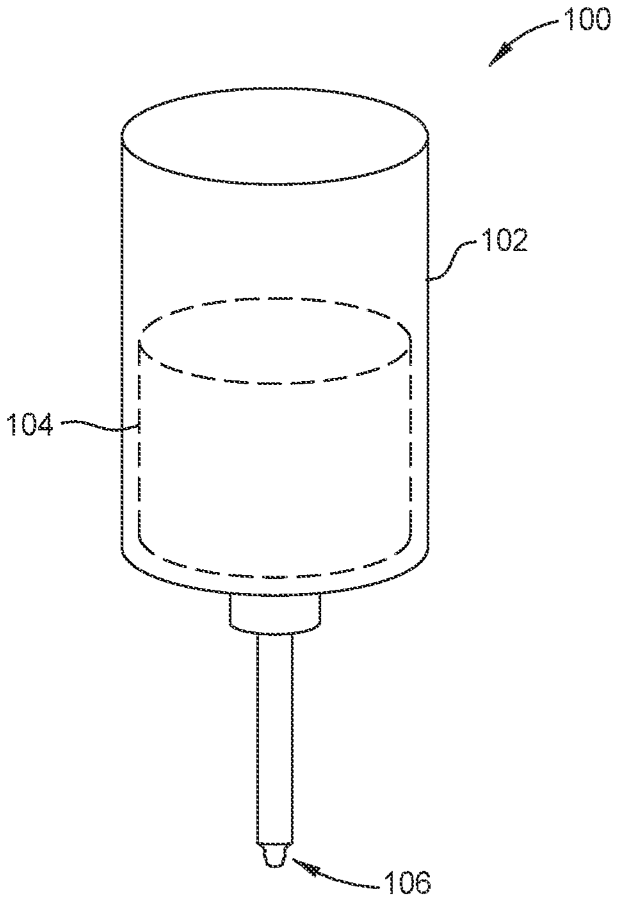
FIG. 1 is an isometric view of an example eye drop dispenser, in accordance with certain embodiments.

Referring to FIG. 1, an eye drop dispenser 100 includes a reservoir 102 containing a fluid 104 to be deposited on a user's eye as droplets. The reservoir 102 may be a flexible squeeze bottle, or other container geometry, such that the pressure within the reservoir 102 increases in response to pressure applied to the exterior of the reservoir 102. Other types of reservoirs may be used, such as those incorporating a pump or other type of mechanism to extract fluid from the reservoir 102 in controlled amounts.

A nozzle 106 is connected to the reservoir. The nozzle 106 is in fluid communication with the interior of the reservoir 102. The nozzle 106 is pressure activated in the sense that the nozzle 106 is sealed and prevents fluid flow in and out of the reservoir 102 in the absence of pressure within the reservoir exceeding a threshold pressure. In response to pressure above the threshold pressure, the fluid 104 is forced out through the nozzle 106 as discussed extensively below. In the description below, "proximal" with reference to the nozzle 106 shall be understood as relatively closer to the reservoir 102 and "distal" with reference to the nozzle 106 shall be understood as relatively further from the reservoir 102.

The fluid within the reservoir 102 may be pressurized by squeezing the reservoir and forcing fluid out of the nozzle 106 as described in detail below. Make-up air to replace the fluid dispensed through the nozzle may, in certain embodiments, be drawn into the reservoir 102 when squeezing of the reservoir ends. Make-up air would be provided without fluid 104 back-flow through the nozzle 106 or contamination of the reservoir 102. In other embodiments, no make-up air is supplied to the reservoir 102.

Referring to FIGS. 2A, 2B, 2C, and 2D, the nozzle 106 incudes a center 200 and a sleeve 202 extending around the center 200. The center 200 defines a longitudinal direction 204*a* that may be defined as one or both of substantially parallel to a longest dimension of the center 200 and parallel to an axis of symmetry or intersection of two or more planes of symmetry of the center 200. A radial direction 204*b* may be defined as perpendicular to and intersecting the longitudinal direction 204*a*. A circumferential direction 204*c* may be defined as circumferential movement or curvature about the longitudinal direction 204*a*.

Figures 2A, 2B, 2C, 2D, 2E:
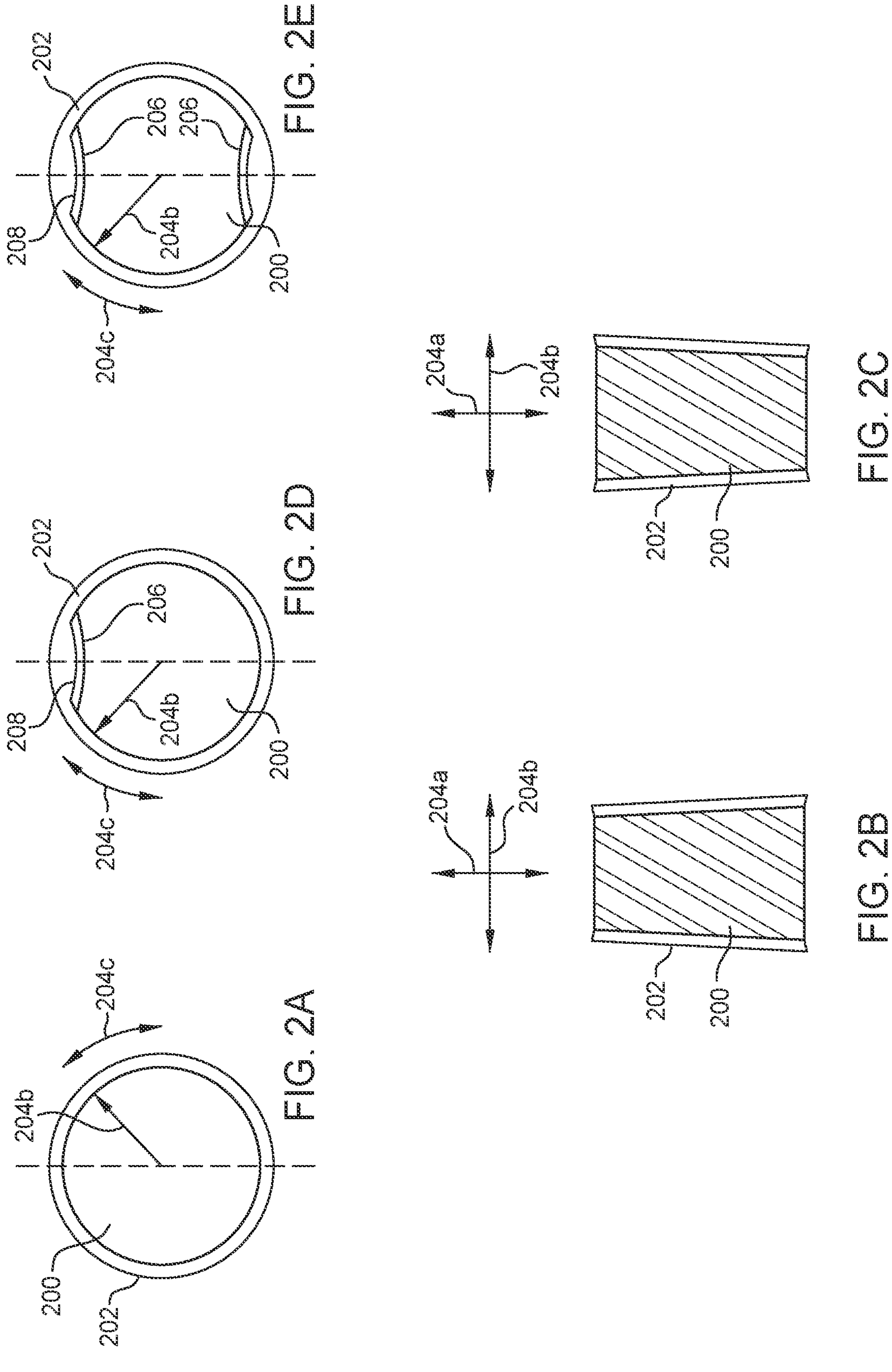
FIGS. 2A to 2E are cross-sectional views of an example nozzle of an eye drop dispenser, in accordance with certain embodiments.

The shape of the center 200 and sleeve 202 are linked, as the resistive pressure of nozzle 106 is proportional to the relative displacement of the sleeve 202 under tension, which is related to the shape, thickness, material, etc., of sleeve 202. In certain embodiments, the center 200 may be defined as a cylinder (FIG. 2A), a frusto-conical shape with a small end thereof distal to the reservoir 102 (e.g., a frustum; FIG. 2B), or a frusto-conical shape with a small end thereof proximal to the reservoir 102 (e.g., a reverse frustum; FIG. 2C). A cylinder and a cone are exemplary only. Other cross-sectional shapes may be used such as elliptical, oval, triangular, square, octagonal, or other polygonal shape. A single longitudinal groove 206 (FIG. 2D) or two or more longitudinal grooves 206 (FIG. 2E) may extend along a side of the center 200 in the longitudinal direction 204*a*. The sleeve 200 may include corresponding one or more ridges 208 that extend into the one or more grooves 206. The grooves 206 may have a concave arcuate cross section in a plane perpendicular to the longitudinal direction 204*a*. Other shapes are possible, such as non-arcuate shapes, a flattened area on an otherwise round center 200, or other shapes. The grooves 206 may become smaller with proximity to the distal end of the center 200 in the case of FIG. 2B or become larger with proximity to the distal end of the center 200 in the case of FIG. 2C. As is apparent, the grooves 206 occupy less than the entire circumference (360°) of the center 200, such as each occupying an angle, e.g., having an angular extent, of less than 180 degrees about the longitudinal direction 204*a*.

The center 200 may be made of a more rigid material than the sleeve 202 whereas the sleeve 202 is made of a flexible material that will expand responsive to pressure within the reservoir 102. Both the center 200 and the sleeve 202 may be made of a plastic material. For example, the sleeve 202 may be made of a flexible elastomer such as silicone whereas the center 200 is made of a rigid polymer such as polyvinyl chloride (PVC), polypropylene, acrylonitrile butadiene styrene (ABS), or other rigid plastic. In other embodiments, a metallic material, such as stainless steel or aluminum, is used for one or both of the center 200 and sleeve 202. Surfaces of the center 200 and/or sleeve 202 in contact with fluid may be treated to control the hydrophilicity or hydrophobicity to aid in prevention of contamination ingress into the reservoir 102 through the nozzle 106.

Referring to FIGS. 3A to 3D, the nozzle 106 may be embodied as the illustrated nozzle 106*a*. FIGS. 3A to 3D show a shape that may be revolved about the longitudinal direction 204*a* to obtain a circular shape. In embodiments including one or more grooves 206 and corresponding ridges 208, the illustrated shape may be located exclusively within the angular extent of each groove 206 in the circumferential direction 204*c*.

In the nozzle 106*a* and other nozzles described herein below with respect to FIGS. 4A to 6D, the sleeve 202 has three zones A, B, and C along the longitudinal direction 204*a*. Each zone has what is referred to herein as an "expansion pressure," which is the pressure required to separate the portion of the sleeve 202 in that zone from the center 200 sufficiently to enable fluid 104 to pass through that zone A, B, or C. These expansion pressures are referred to herein as $P_A$, $P_B$, and $P_C$, for zones A, B, and C, respectively. In the nozzle 106*a*, and possibly the other embodiments of the nozzle 106 disclosed herein, $P_A > P_B > P_C$. The different expansion pressures $P_A$, $P_B$, and $P_C$ may be achieved by using different thicknesses for the center 200 and/or sleeve 202 in the radial direction 204*b* in the different zones A, B, C. The thickness of each zone A, B, C may vary such that $P_A$, $P_B$, and $P_C$ may be defined as the average expansion pressure within a zone, the minimum expansion pressure within a zone, or the expansion pressure at a center point of each zone. Other approaches for achieving different expansion pressures may also be used, such as adding bands of material around the sleeve 202, using different materials or material combinations for different zones A, B, C, or other approaches.

Zone B acts as a "living hinge" about which zone C can pivot (e.g., expand or contract) without substantially affecting zone A. As described in detail below, the illustrated geometry facilitates cutting off fluid flow through zone A while fluid is still flowing out of zones B and C, thereby eliminating the possibility that fluid will flow back into the reservoir 102.

Figure 3A:
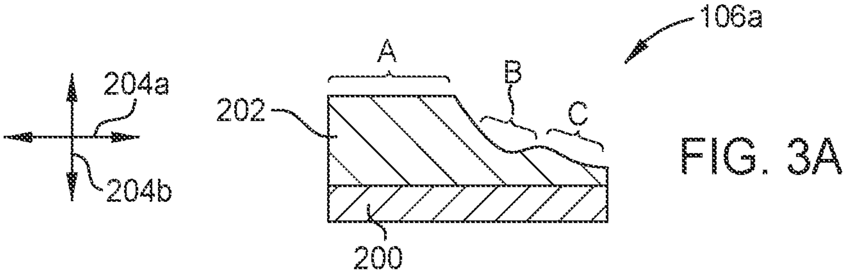
FIGS. 3A to 3D are cross sectional views illustrating an example nozzle, in accordance with certain embodiments.
Figure 3B:
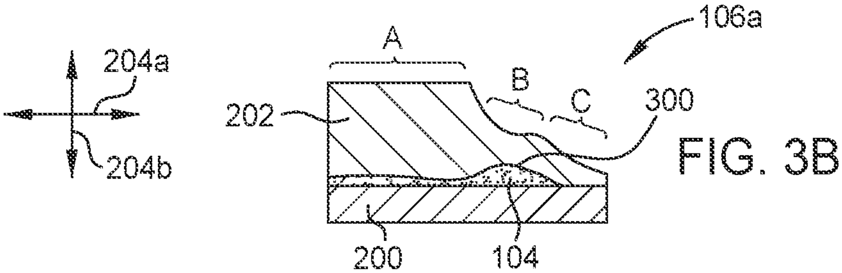
Figure 3C:
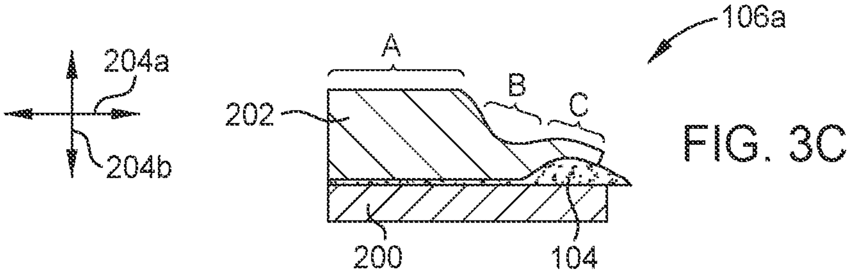

Referring to FIG. 3B, as pressure in the reservoir 102 is increased, zone A expands and transports fluid 104 upon the pressure reaching at least $P_A$. Zone B collects the fluid 104 in a chamber 300. The chamber 300 may be present in the absence of fluid 104 in zone B or may result from expansion of zone B responsive to the pressure of the fluid 104. As the chamber 300 expands and fills with fluid 104, the fluid 104 exerts a force on zone B in the radial direction 204*b*, which is at least partially transferred to zone C, thereby reducing the contact pressure (inward pressure exerted by the sleeve 202 on the center 200) exerted in zone C to below $P_C$. Pressure in the chamber 300 increases and the contact pressure in zone C decreases until zone C separates from the center 200 and the fluid 104 is allowed to flow out of the nozzle 106*a*, as shown in FIG. 3C.

While the fluid 104 is being dispensed from the nozzle 106*a*, the geometry of the interior of zones A, B and C is such that there is a section of accelerated fluid flow at the transition between zone A and zone B that causes high fluid shear, thereby reducing and substantially preventing any flow back upstream into the reservoir 102.

Figure 3D:
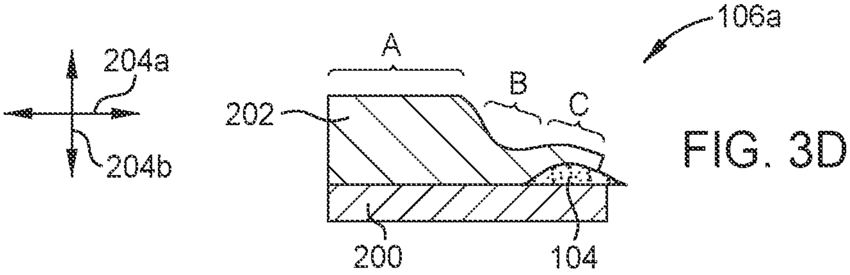

Referring to FIG. 3D, when pressure in the reservoir falls such that the pressure in zone A is below $P_A$, zone A collapses against the center 200 and stops fluid flow from the reservoir 102 and prevents backward flow. As this occurs, zones B and C are momentarily still at sufficiently high pressure to permit fluid flow after zone A has collapsed and fluid 104 continues to flow out of the distal end of the nozzle 106*a* until the pressure in zones B and C drops below $P_B$, and $P_C$, respectively. The living hinge of zone B may be designed in such a way that as zone C is closing, zone B continues to dispense the fluid 104 through zone AC at a high velocity and shear flow up to the moment of closure of zone C, which further prevents backflow into zone A, thereby reducing or substantially eliminating the possibility of contamination of the fluid 104 in the reservoir 102.

The collapsing of zones B and C may result in a high velocity of exiting fluid 104 that facilitates detachment of any drops from an end of the nozzle 106*a*. Where the center 200 has a frusto-conical shape that narrows with distance from the reservoir, the reduced size at the tip of the nozzle 106*a* may further facilitate releasing of drops from the nozzle 106*a*. In other embodiments, a reverse frustum (see FIG. 2C) is used to provide a blunt end facing the user's eye. The sleeve 202 extending around the center 200 increases the diameter of the tip of the nozzle thereby reducing risk associated with having a frusto-conical center 200 with a small tip facing the eye during use. The distal end of center 200 may have a hydrophobic surface (e.g., surface texture, surface coating, or nanotechnology) to further facilitate releasing of drops.

In certain embodiments, additional features may be introduced between the reservoir 102 and the nozzle 106*a*. For example, a pressure-dependent valve on the center 200 and/or sleeve 202 may ensure that fluid flow out of the reservoir 102 does not begin until pressure in the reservoir 102 exceeds a threshold pressure such as a pressure greater than $P_A$. The pressure-dependent valve may further ensure a high shear flow when flow commences. The pressure dependent valve may be implemented as a barb, detent, another type of valve, or according to any of the embodiments for the nozzle described herein.

Referring to FIGS. 4A to 4E, the nozzle 106 may be implemented as the illustrated nozzle 106*b*. FIGS. 4A to 4E show a shape that may be revolved about the longitudinal direction 204*a* to obtain a circular shape. In embodiments including one or more grooves 206 and corresponding one or more ridges 208, the illustrated shape may be located exclusively within the angular extent of the groove 206 in the circumferential direction 204*c*.

Figure 4A:
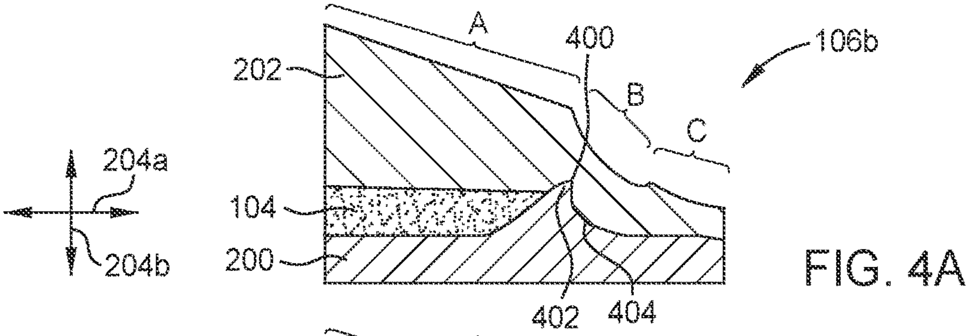
FIGS. 4A to 4E are cross sectional views illustrating another example nozzle, in accordance with certain embodiments.

In the nozzle 106*b*, the sleeve 202 defines a notch 400 and the center 200 defines a ridge 402 that sits within the notch 400. Various cross-sectional shapes may be used for the ridge 402, such as hemispherical elliptical, triangular, or other more complex shape. As shown in FIG. 4A, there may be a fillet 404 defining a gradual transition from the peak of the ridge 402 to the reduced diameter of the center 200 at the distal end of the nozzle 106*b*.

The arrangement of the notch 400 and ridge 402 may be reversed: the center 200 may define the notch 400 whereas the sleeve 202 defines an inwardly extending ridge 402. The ridge 402 may be located at a transition between zone A and zone B. As is apparent, there may be gradual changes in thickness of the sleeve 202 between the zones A, B, and C. The diameter of the center 200 may also change between zones A, B, and C. The ridge 402 and notch 400 may therefore be positioned along the longitudinal direction 204*a* in the transition between zone A and zone B. Stated differently, zone B may have a point along the longitudinal direction 102*a* having a minimum thickness measured in the radial direction 204*b* between the greater thicknesses of zones A and C. In addition, the sleeve 202 can have an equivalent thickness across this range, decreasing from zone A, to zone B, to zone C, or alternatively, increasing from zone A, to zone B, to zone C.

The notch 400 and ridge 402 may be located proximally from that point of minimum thickness by between 1 and 5 mm (millimeters).

Figure 4B:
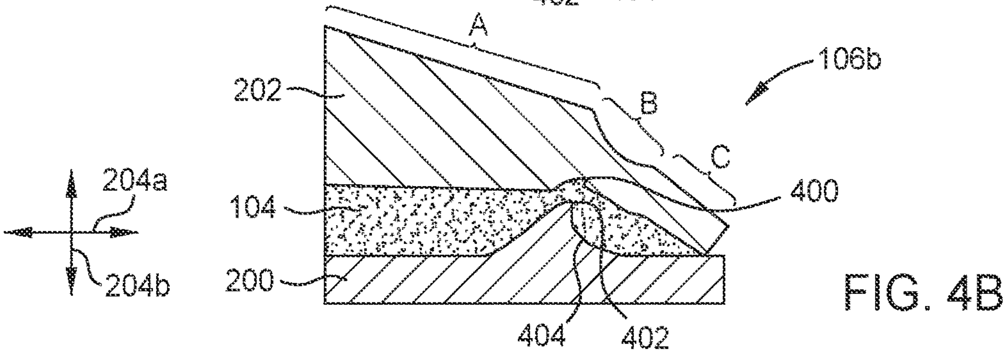
Figure 4C:
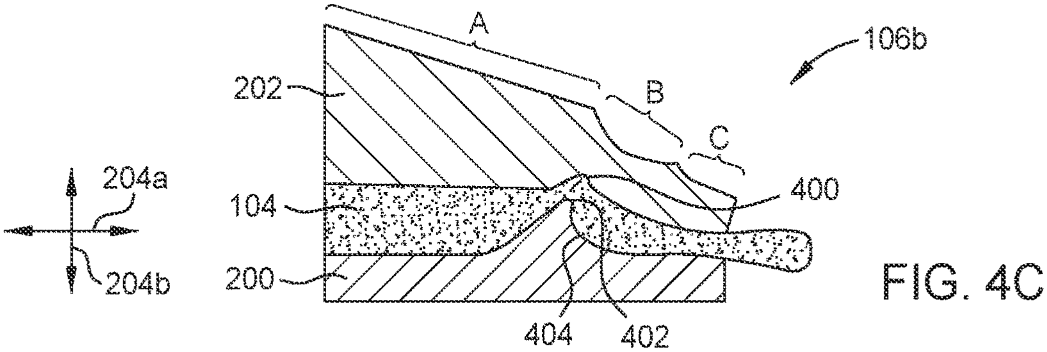

Referring to FIG. 4A, when the user increases pressure in the reservoir 102, the fluid 104 is forced into zone A. The pressure in zone A increases until the sleeve 202 separates from the center 200 sufficient to separate the notch 400 from the ridge 402 and fluid begins to flow into zone B as shown in FIG. 4B. The constriction between the notch 400 and the ridge 402 causes high fluid velocity and sheer throughout the duration of fluid flow, reducing and preferably preventing backflow. As the fluid 104 continues to flow into zone B, pressure in zone B increase and zone B is raised, thereby lowering the contact pressure in zone A until zone A separates from the center 200 and fluid flows out of the nozzle 106*b* as shown in FIG. 4C.

Figure 4D:
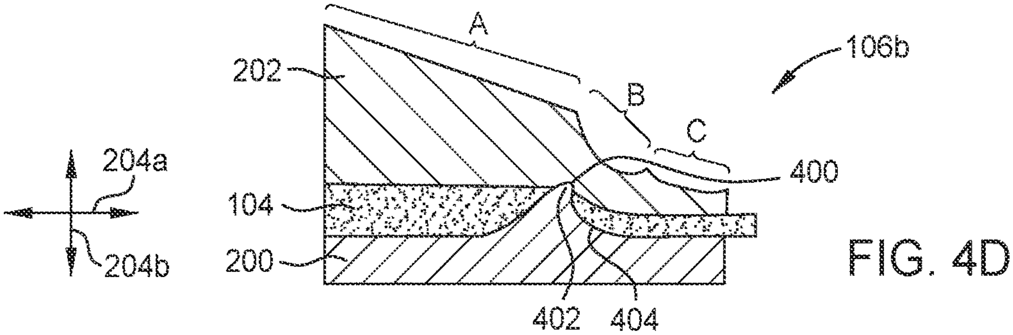

Referring to FIG. 4D, when the pressure in the reservoir 102 drops below the pressure required to separate the notch 400 and the ridge 402, the sleeve 202 collapses and presses the notch 400 and ridge 402 together, hindering and substantially preventing further fluid flow from the reservoir 102 and preventing backflow. As this occurs, zones B and C are momentarily still at sufficiently high pressure to permit fluid flow after zone A has collapsed and fluid 104 continues to flow out of the distal end of the nozzle 106*b* until the pressure in zones B and C drops below $P_B$, and $P_C$. The nozzle 106*b* may then return to the state shown in FIG. 4A. In the state shown in FIG. 4A, some or all of zone B and/or some or all of zone C nest in the fillet 404 and expel substantially all fluid in the portion of the nozzle 106*b* that is distal of the notch 400 and creating a tight interface of sufficient tension to prevent contamination influx. As mentioned above, in this and all other embodiments, material selection or surface treatments to the center 200 and the sleeve 202 may be used to control the hydrophilicity or hydrophobicity of surfaces contacting dispensed fluid. This may aid in the prevention of contamination ingress by causing the displacement of fluid in the areas of contact between the center 200 and the sleeve 202, particularly in the area of notch 400 and ridge 402.

Figure 4E:
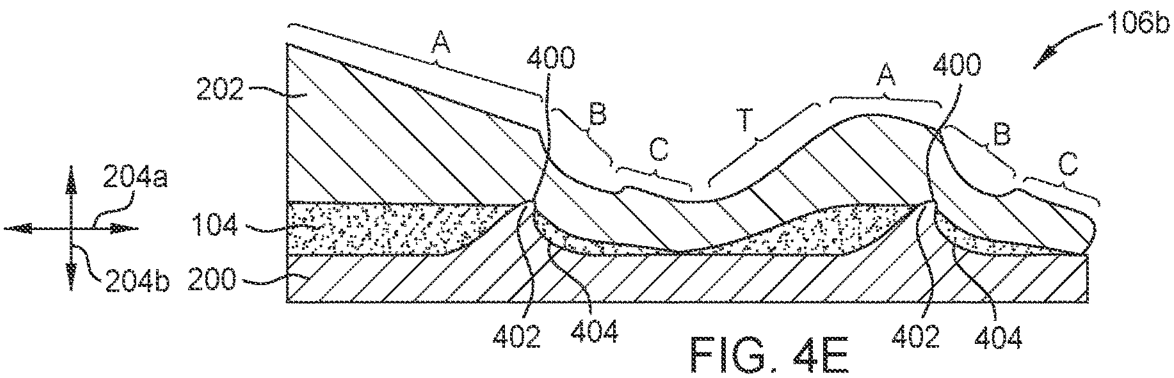

Referring to FIG. 4E, there may be multiple instances of the nozzle 106*b* arranged in series along the longitudinal direction 204*a*. Accordingly, moving from proximal to distal there may be a zone A, a zone B, a zone C, a transition region T, and other instances of a zone A, a zone B, and a zone C, and so on for zero or more additional instances. Two instances are shown but there may be any number, such as three, four, or more instances. The instances may be identical to one another (within manufacturing tolerances) or may be intentionally made unequal with $P_A$, $P_B$, and $P_C$ of one instance being different from those of another instance. There may be multiple instances of any of the embodiments of the nozzle 106 described herein. There may be multiple instances of the same embodiment of the nozzle 106 or there may be multiple different embodiments of the nozzle 106 arranged in series. Where multiple instances are used, the instances may open sequentially from proximal to distal and likewise collapse in sequence from proximal to distal.

Referring to FIGS. 5A to 5E, the nozzle 106 may be implemented as the illustrated nozzle 106*c*. FIGS. 5A to 5E show a shape that may be revolved about the longitudinal direction 204*a* to obtain a circular shape. In embodiments including one or more grooves 206 and corresponding one or more ridges 208, the illustrated shape may be located exclusively within the angular extent of the groove 206 in the circumferential direction 204*c*.

Figure 5A:
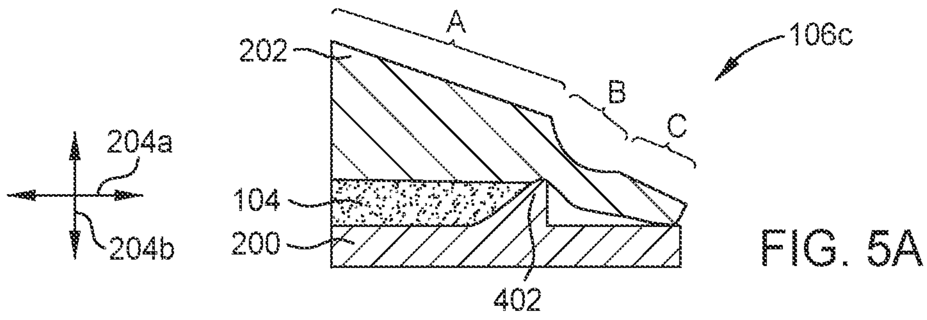
FIGS. 5A to 5E are cross sectional views illustrating another example nozzle, in accordance with certain embodiments.
Figure 5B:
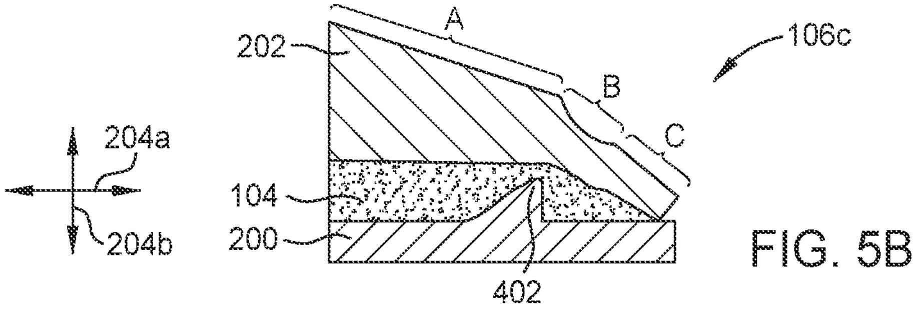
Figure 5C:
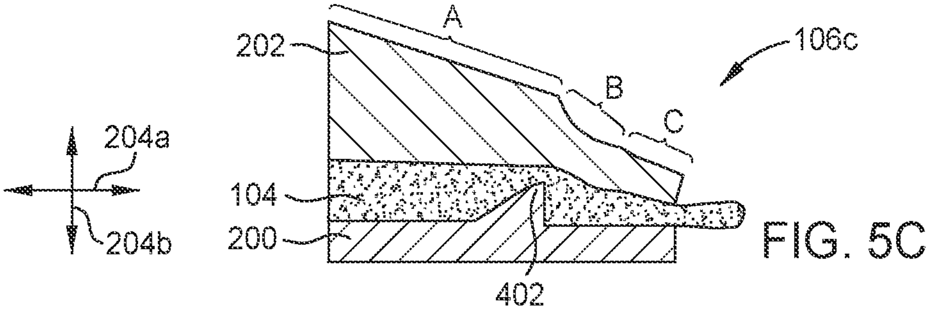
Figure 5D:
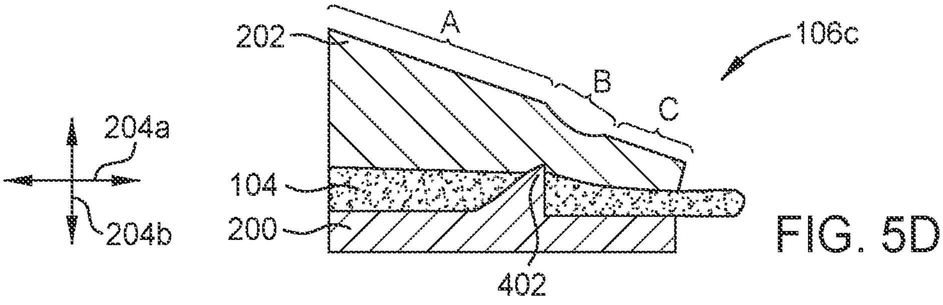
Figure 5E:
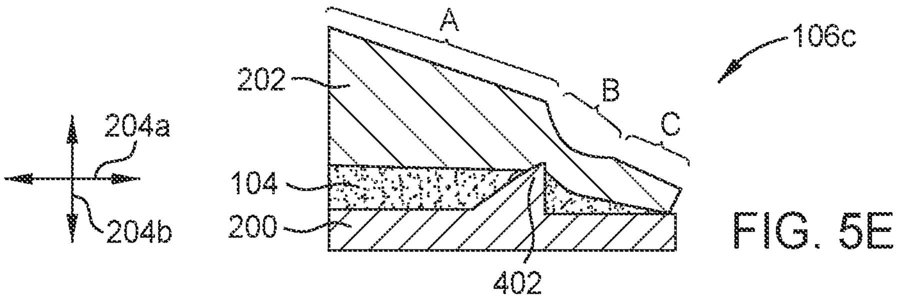

The nozzle 106*c* may have the features of the nozzle 106*b* except that the sleeve 202 lacks a notch 400 in the sleeve 202 while the ridge 402 on the center 200 is retained. In the nozzle 106*c*, the fillet 404 may also be retained or omitted. The perpendicular face on the distal side of the ridge 402 may have the advantage of increasing local turbulence. As shown in FIGS. 5A to 5E, the nozzle 106*c* may operate in the same manner as the nozzle 106*b*. In particular, the high velocity and sheer may still be present between the ridge 402 and the sleeve 202 without the notch as shown in FIG. 5B. With the fillet 404 absent, some fluid 104 may be trapped between the sleeve 202 and the center 200 distal of the ridge 402 following use as shown in FIG. 5E. Accordingly, in such embodiments, a purging step may be performed by the user in which fluid 104 is expelled from the nozzle 106*c* and discarded before applying drops to the user's eye. In some embodiments, the notch 400 is omitted while retaining the ridge 402 on either the center 200 or on the sleeve 202, as described above with respect to FIGS. 4A-4D above.

Referring to FIGS. 6A to 6D, the nozzle 106 may be implemented as the illustrated nozzle 106*d*. FIGS. 5A to 5E show a shape that may be revolved about the longitudinal direction 204*a* to obtain a circular shape. In embodiments including one or more grooves 206 and corresponding one or more ridges 208, the illustrated shape may be located exclusively within the angular extent of the groove 206 in the circumferential direction 204*c*.

In the nozzle 106*d*, zone C includes a flow acceleration feature 600. The acceleration feature may be implemented as one or more sharp points in zone C that contact the center 200. For example, the flow acceleration feature 600 may have a tip 602 having a radius of curvature of less than 1 mm, less than 0.5 mm, or less than 0.2 mm.

Figure 6A:
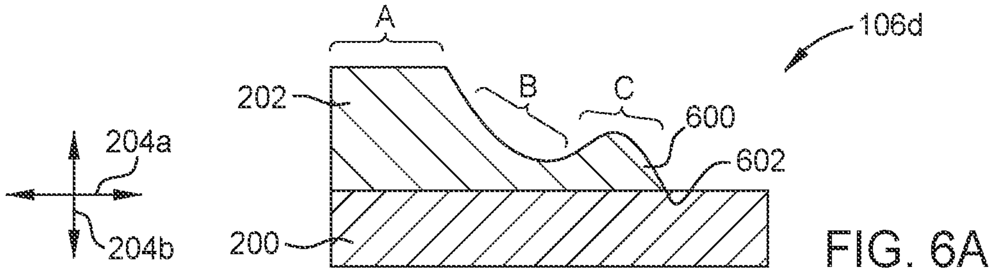
FIGS. 6A to 6D are cross sectional views illustrating another example nozzle, in accordance with certain embodiments.
Figure 6B:
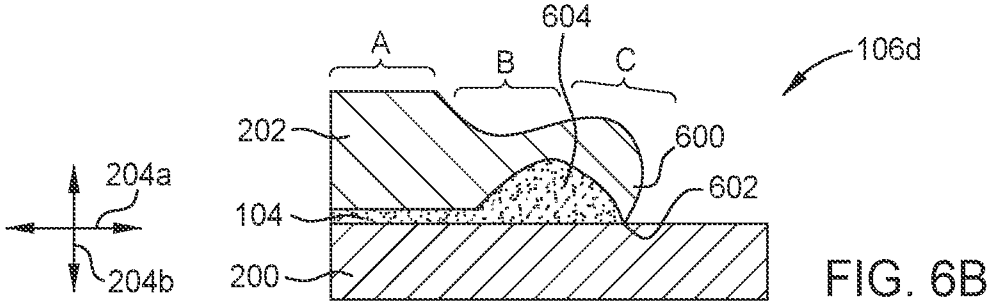
Figure 6C:
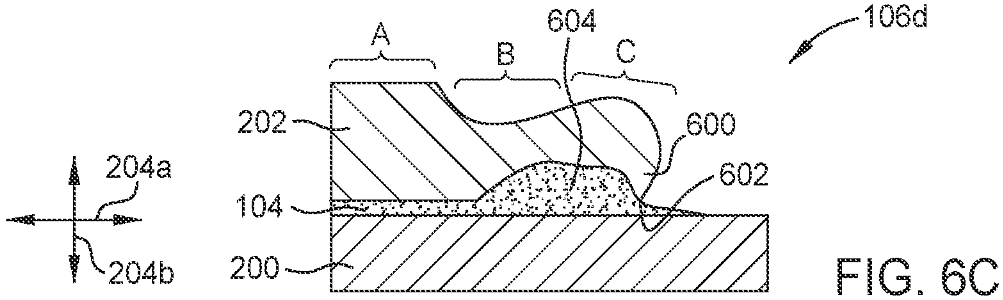

As shown in FIG. 6B, as the pressure in zone A rises above $P_A$, fluid 104 is forced into zone B and zone B expands to form a chamber 604 between the sleeve 202 and the center 200. The flow acceleration feature 600 may remain in contact with the center 200 as the chamber 604 fills. As for other embodiments, the living hinge in zone B causes zone B to rise above the center 200 and lower the contact pressure of zone C, including the acceleration feature 600 until the contact pressure of zone C falls below the pressure in the chamber 604 and fluid exits zone C as shown in FIG. 6C. The presence of the flow acceleration feature 600 ensures that fluid 104 exits the chamber 604 at high speed, thereby reducing the risk of backflow into the reservoir 102.

Figure 6D:
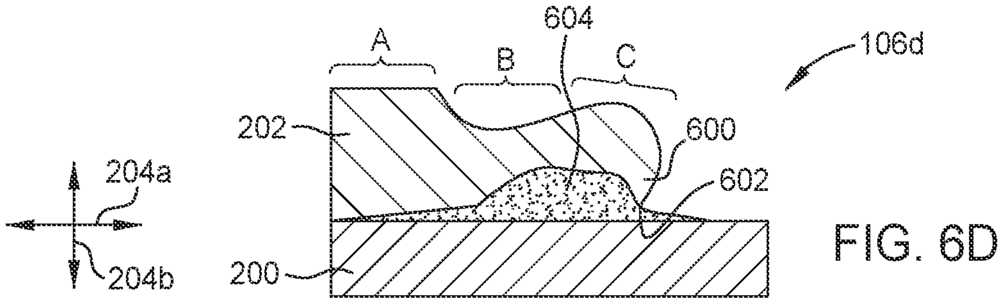

As shown in FIG. 6D, when pressure in the reservoir 102 drops, zone A collapses first. As this occurs, zones B and C are momentarily still at sufficiently high pressure to permit fluid flow after zone A has collapsed. As the living hinge of zone B collapses, the chamber 604 empties and fluid 104 continues to flow out of the distal end of the nozzle 106 until the pressure in zones B and C drops below $P_B$, and $P_C$. The acceleration feature 600 ensures that this continued flow is at a sufficiently high flow rate and shear to prevent entry of contaminants into the nozzle 106*d*.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A nozzle for an eye dropper comprising:

a center configured to affix to a reservoir at a proximal end of the center and having a distal end opposite the proximal end;

a sleeve extending around the center and having a first zone, a second zone, and a third zone, the first zone being positioned closer to the proximal end than the second zone and the third zone being positioned closer to the distal end than the second zone;

wherein at least a portion of the first zone has a first expansion pressure at which the at least the portion of the first zone will separate from the center such that fluid can flow between the at least the portion of the first zone and the center;

wherein at least a portion of the second zone has a second expansion pressure at which the at least the portion of the second zone will separate from the center such that the fluid can flow between the at least the portion of the second zone and the center;

wherein at least a portion of the third zone has a third expansion pressure at which the at least the portion of the third zone will separate from the center such that the fluid can flow between the at least the portion of the third zone and the center;

wherein the second expansion pressure is less than the first expansion pressure; and wherein the at least the portion of the first zone has a first thickness extending outwardly from the center, the at least the portion of the second zone has a second thickness extending outwardly from the center, and the at least the portion of the third zone has a third thickness, the third thickness being less than at least one of the first thickness or the second thickness.

2. The nozzle of claim 1, wherein the sleeve is made of a more flexible material than the center.

3. The nozzle of claim 1, wherein the center is cylindrical.

4. The nozzle of claim 1, wherein the center has a frusto-conical shape.

5. The nozzle of claim 1, wherein the center has one or more grooves extending from the distal end at least partially to the proximal end, the first zone, second zone, and third zone being located exclusively over the one or more grooves.

6. The nozzle of claim 1, wherein the third expansion pressure is less than the second expansion pressure.

7. The nozzle of claim 1, wherein the second thickness is less than the first thickness.

8. The nozzle of claim 1, wherein one of:

(a) a ridge is formed on the center and a groove is formed on within the sleeve and positioned to receive the ridge; and (b) a ridge is formed on the sleeve and a groove is formed on within the center and positioned to receive the ridge.

9. The nozzle of claim 8, further comprising a fillet extending distally from the ridge, the third zone being configured to seat against the fillet.

10. The nozzle of claim 1, wherein the third zone includes an acceleration feature.

11. The nozzle of claim 10, wherein the acceleration feature includes a peak configured to press against the center, the peak having a tip with a radius of curvature of less than 1 mm (millimeter).

12. A nozzle for an eye dropper comprising:

a first zone, a second zone, and a third zone, the second zone being between the first zone and the third zone and the first zone configured to receive fluid from a reservoir, the first zone, second zone, and third zone configured such that:

(a) in response to pressurization of the fluid from the reservoir:

(i) the fluid overcomes a first expansion pressure of the first zone and the fluid flows through the first zone;

(ii) the fluid overcomes a second expansion pressure of the second zone such that the fluid flows into the second zone and expands the second zone to form a chamber; and (iii) the fluid overcomes a third expansion pressure of the third zone in combination with expansion of the third zone induced by expansion of the second zone and causes the fluid to flow through the third zone; and (b) in response to depressurization of the fluid from the reservoir:

(iv) the first zone collapses; and (v) following (iv), the fluid continues to flow out of the second zone and the third zone such that backflow into the reservoir is reduced; and wherein the at least the portion of the first zone has a first thickness extending outwardly from the center, the at least the portion of the second zone has a second thickness extending outwardly from the center, and the at least the portion of the third zone has a third thickness, the third thickness being less than at least one of the first thickness or the second thickness.

13. The nozzle of claim 12, wherein the nozzle is configured such that (ii) occurs after (i) and (iii) occurs after (ii).

14. The nozzle of claim 12, wherein the first expansion pressure is greater than the second expansion pressure.

* * * * *